United States Patent
Kang et al.

(10) Patent No.: US 8,236,520 B2
(45) Date of Patent: Aug. 7, 2012

(54) **RECOMBINANT BETA-GALACTOSIDASE DERIVED FROM *STREPTOCOCCUS PNEUMONIAE***

(75) Inventors: Hyun Ah Kang, Daejeon (KR); Jae Kap Jeong, Daejeon (KR); Ohsuk Kwon, Daejeon (KR); Doo-Byoung Oh, Daejeon (KR); Seonghun Kim, Daejeon (KR)

(73) Assignee: Korea Research Institute of Bioscience and Biotechnology, Daejeon (KR)

( * ) Notice: Subject to any disclaimer, the term of this patent is extended or adjusted under 35 U.S.C. 154(b) by 0 days.

(21) Appl. No.: 12/952,116

(22) Filed: Nov. 22, 2010

(65) Prior Publication Data

US 2011/0287463 A1    Nov. 24, 2011

Related U.S. Application Data

(62) Division of application No. 11/823,333, filed on Jun. 25, 2007, now abandoned.

(30) Foreign Application Priority Data

Jun. 23, 2006 (KR) .......... 10-2006-0057140

(51) Int. Cl.
C12Q 1/34 (2006.01)
C12N 9/38 (2006.01)
(52) U.S. Cl. ................... 435/18; 435/207
(58) Field of Classification Search .......... None
See application file for complete search history.

(56) References Cited

OTHER PUBLICATIONS

Online Database NCBI "Beta-Galactosidase 3 *Streptococcus pneumoniae*" Published on (Sep. 6, 2001) (2 Pgs).
Online Database NCBI "*Streptococcus pneumoniae* R6 Section 6 of 184 of the Complete Genome" Published on (Sep. 3, 2001) (6 Pgs).
Greenburg and Mahoney, "Immobilisation of Lactase (BGalactosidase) for use in Dairy Processing: A Review" 1981 Process Biochem. 16:2-8.
Gekas and Lopez-Levia, "Hydrolysis of Lactose: A Literature Review" 1985 Process Biochem. 20:2-12.
Takada et al., "Contribution of Carbohydrate Antigens Sialyl Lewis A and Sialyl Lewis X to Adhesion of Human Cancer Cells to Vascular Endothelium" 1993 Cancer Res. 53:354-361.
Zahner and Hakenberck, "The *Streptococcus pneumoniae* Beta-Galactosidase Is a Surface Protein" 2000 J. Bacteriol 182:5919-5921.
Glasgow et al., "Systematic Purification of Five Glycosidases from *Streptococcus (Diplococcus) pneumoniae*" 1977 J. Biol. Chem. 252:8615-8623.
Hughes and Jeanloz, "The Extracellular Glycosidases of *Diplococcus pneumoniae*. I. Purification and Properties of a Neuraminidase and a iJ-Galactosidase. Action on the (XI-Acid Glycoprotein of Human Plasma" 1964 Biochemistry 10:1535-1548.
Hoskins et al., "Genome of the Bacterium *Streptococcus pneumoniae* Strain R6" 2001 J. Bacteriol. 183:5709-5712.
Arcaro et al, "B-Galactosidase and A-Mannosidase Inhibit Fromation of Multicellular Nodules in Breast Cancer Cell Cultures," Anticancer Research, 2004, vol. 24, p. 139-144.
UniProKB Accession No: Q8DRL4 Mar. 1, 2003. (12 Pgs).

*Primary Examiner* — Tekchand Saidha
*Assistant Examiner* — Md. Younus Meah
(74) *Attorney, Agent, or Firm* — Casimir Jones SC

(57) ABSTRACT

The present invention relates to beta-galactosidase derived from *Streptococcus pneumoniae*, a BgaC protein exhibiting the enzyme activity, and a method for using the same. The protein can be used in the modification and analysis of sugar chain and used as an anti-cancer agent.

4 Claims, 8 Drawing Sheets

− BgaC

+ BgaC

```
                        SEQUENCE LISTING

<160> NUMBER OF SEQ ID NOS: 4

<210> SEQ ID NO 1
<211> LENGTH: 1788
<212> TYPE: DNA
<213> ORGANISM: Streptococcus pneumoniae

<400> SEQUENCE: 1
atgacacgat ttgagatacg agatgatttc tatctcgatg gaaaatcatt taagatttta      60
tctggtgcca ttcattattt taggattcct ccagaggatt ggtatcattc gctctataac     120
ttgaaggctc ttggtttaa tacggtagag acttatgttg cttggaattt acacgagcct     180
cgtgaaggtg agtttcattt tgaaggtgat ctggatttag agaaatttct ccaaatagcg     240
caggatttgg gtctctacgc aattgtgcgt ccgtctccat ttatctgtgc ggaatgggaa     300
ttcggtggct taccagcttg gctcttgacc aagaacatgc gaattcgctc atccgaccca     360
gcatatatcg aggcagttgg tcgctactat gatcagttat tgccaagact ggtgcctcgt     420
ttgttgaaca atggtggcaa tattctcatg atgcaggttg aaaatgagta tggttcttac     480
ggagaagata aggcttacct gagagcgatt cgacagctaa tggaagagtg tggcgtaacc     540 tgtccctct  ttacatcaga tggtccatgg cgagctactc tgaaagctgg aaccttaatt     600
gaagaggacc tctttgtaac aggaaacttt ggttctaagg caccttacaa cttttcgcag     660
atgcaggaat tcttttgatga acatggtaag aaatggccac tcatgtgtat ggagttctgg     720
gatggttggt tcaatcgctg gaaagaaccg attatcacac gggatcctaa ggaattggca     780
gatgcagttc gagaggtttt ggaacaaggc tctatcaatc tttacatgtt ccacggtggt     840
gcaaactttg gtttcatgaa tggttgctca gctcgaggaa ctttggacct gccacaagtt     900
acatcttatg attacgatgc ccttctggat gaagaaggaa atccaactgc taaatatctt     960
gcagtcaaga agatgatggc aacacatttt tcagagtatc cgcagttgga accactctac    1020
aaagagagta tggagttgga tgctattcca ctagttgaaa aagtttcttt gtttgaaacc    1080
ttagatagct tgtcaagtcc tgtagaaagt ctctatcctc aaaagatgga ggagctggga    1140
```

```
caaagttatg ctacctact ttatcgaaca gaaacaaact gggatgcaga agaagaaaga      1200
cttcgtatca ttgatggtcg agatagggcc cagctgtatg tcgatggtca gtgggttaaa      1260
actcaatatc agacagagat tggggaagat attttttatc aaggtaaaaa gaaagggcta      1320
tctaggttag atatcttgat agaaaatatg gggcgtgtca actatgggca taagttctta      1380
gcggatacgc aacgtaaggg aattcggaca ggggtctgta aggatctgca tttcttacta      1440
aactggaaac actatccact cccactagac aatcctgaga aaattgattt ttcaaaagga      1500
tggactcaag acaaccagc cttttacgct tatgacttta cagtcgaaga gccaaaagat      1560
acttacctag acttgtctga gtttggtaag ggagttgcct ttgtcaatgg cagaatcta      1620 ggacgttttt ggaacgttgg cccaactctc tcactttata tccctcatag ctatctcaag      1680
gaaggtgcca accgtatcat tatctttgaa acagaaggtc aatataaaga agagattcat      1740
ttaactcgta aacctacact aaaacatata aagggggaaa acttatga               1788
```

<210> SEQ ID NO 2
<211> LENGTH: 595
<212> TYPE: PRT
<213> ORGANISM: Streptococcus pneumoniae

<400> SEQUENCE: 2

```
Met Thr Arg Phe Glu Ile Arg Asp Asp Phe Tyr Leu Asp Gly Lys Ser
1               5                   10                  15

Phe Lys Ile Leu Ser Gly Ala Ile His Tyr Phe Arg Ile Pro Pro Glu
            20                  25                  30

Asp Trp Tyr His Ser Leu Tyr Asn Leu Lys Ala Leu Gly Phe Asn Thr
        35                  40                  45

Val Glu Thr Tyr Val Ala Trp Asn Leu His Glu Pro Arg Glu Gly Glu
    50                  55                  60

Phe His Phe Glu Gly Asp Leu Asp Leu Glu Lys Phe Leu Gln Ile Ala
65                  70                  75                  80

Gln Asp Leu Gly Leu Tyr Ala Ile Val Arg Pro Ser Pro Phe Ile Cys
                85                  90                  95

Ala Glu Trp Glu Phe Gly Gly Leu Pro Ala Trp Leu Leu Thr Lys Asn
            100                 105                 110

Met Arg Ile Arg Ser Ser Asp Pro Ala Tyr Ile Glu Ala Val Gly Arg
        115                 120                 125

Tyr Tyr Asp Gln Leu Leu Pro Arg Leu Val Pro Arg Leu Leu Asn Asn
    130                 135                 140

Gly Gly Asn Ile Leu Met Met Gln Val Glu Asn Glu Tyr Gly Ser Tyr
145                 150                 155                 160

Gly Glu Asp Lys Ala Tyr Leu Arg Ala Ile Arg Gln Leu Met Glu Glu
                165                 170                 175

Cys Gly Val Thr Cys Pro Leu Phe Thr Ser Asp Gly Pro Trp Arg Ala
            180                 185                 190

Thr Leu Lys Ala Gly Thr Leu Ile Glu Glu Asp Leu Phe Val Thr Gly
        195                 200                 205

Asn Phe Gly Ser Lys Ala Pro Tyr Asn Phe Ser Gln Met Gln Glu Phe
    210                 215                 220

Phe Asp Glu His Gly Lys Lys Trp Pro Leu Met Cys Met Glu Phe Trp
225                 230                 235                 240

Asp Gly Trp Phe Asn Arg Trp Lys Glu Pro Ile Ile Thr Arg Asp Pro
                245                 250                 255

Lys Glu Leu Ala Asp Ala Val Arg Glu Val Leu Glu Gln Gly Ser Ile
            260                 265                 270
```

```
Asn Leu Tyr Met Phe His Gly Gly Ala Asn Phe Gly Phe Met Asn Gly
        275                 280                 285
Cys Ser Ala Arg Gly Thr Leu Asp Leu Pro Gln Val Thr Ser Tyr Asp
        290                 295                 300
Tyr Asp Ala Leu Leu Asp Glu Glu Gly Asn Pro Thr Ala Lys Tyr Leu
305                 310                 315                 320
Ala Val Lys Lys Met Met Ala Thr His Phe Ser Glu Tyr Pro Gln Leu
                325                 330                 335
Glu Pro Leu Tyr Lys Glu Ser Met Glu Leu Asp Ala Ile Pro Leu Val
                340                 345                 350
Glu Lys Val Ser Leu Phe Glu Thr Leu Asp Ser Leu Ser Ser Pro Val
                355                 360                 365
Glu Ser Leu Tyr Pro Gln Lys Met Glu Glu Leu Gly Gln Ser Tyr Gly
                370                 375                 380
Tyr Leu Leu Tyr Arg Thr Glu Thr Asn Trp Asp Ala Glu Glu Glu Arg
385                 390                 395                 400
Leu Arg Ile Ile Asp Gly Arg Asp Arg Ala Gln Leu Tyr Val Asp Gly
                405                 410                 415
Gln Trp Val Lys Thr Gln Tyr Gln Thr Glu Ile Gly Glu Asp Ile Phe
                420                 425                 430
Tyr Gln Gly Lys Lys Gly Leu Ser Arg Leu Asp Ile Leu Ile Glu
                435                 440                 445
Asn Met Gly Arg Val Asn Tyr Gly His Lys Phe Leu Ala Asp Thr Gln
        450                 455                 460
Arg Lys Gly Ile Arg Thr Gly Val Cys Lys Asp Leu His Phe Leu Leu
465                 470                 475                 480
Asn Trp Lys His Tyr Pro Leu Pro Leu Asp Asn Pro Glu Lys Ile Asp
                485                 490                 495
Phe Ser Lys Gly Trp Thr Gln Gly Gln Pro Ala Phe Tyr Ala Tyr Asp
                500                 505                 510
Phe Thr Val Glu Glu Pro Lys Asp Thr Tyr Leu Asp Leu Ser Glu Phe
                515                 520                 525
Gly Lys Gly Val Ala Phe Val Asn Gly Gln Asn Leu Gly Arg Phe Trp
                530                 535                 540
Asn Val Gly Pro Thr Leu Ser Leu Tyr Ile Pro His Ser Tyr Leu Lys
545                 550                 555                 560
Glu Gly Ala Asn Arg Ile Ile Ile Phe Glu Thr Glu Gly Gln Tyr Lys
                565                 570                 575
Glu Glu Ile His Leu Thr Arg Lys Pro Thr Leu Lys His Ile Lys Gly
                580                 585                 590
Glu Asn Leu
    595

<210> SEQ ID NO 3
<211> LENGTH: 29
<212> TYPE: DNA
<213> ORGANISM: Artificial Sequence
<220> FEATURE:
<223> OTHER INFORMATION: Synthetic

<400> SEQUENCE: 3
cgctagcatg acacgatttg agatacgag                                    29

<210> SEQ ID NO 4
<211> LENGTH: 32
<212> TYPE: DNA
```

-continued

```
<213> ORGANISM: Artificial Sequence
<220> FEATURE:
<223> OTHER INFORMATION: Synthetic

<400> SEQUENCE: 4
ggaagctttc ataagttttc cccctttata tg                                        32
```

RECOMBINANT BETA-GALACTOSIDASE DERIVED FROM *STREPTOCOCCUS PNEUMONIAE*

CROSS REFERENCE TO RELATED APPLICATIONS

This application is a divisional of U.S. patent application Ser. No. 11/823,333, filed: Jun. 25, 2007, which claims priority to Korean Patent Application Serial No.: KR 10-2006-0057140, filed: Jun. 23, 2006, both of which are herein incorporated by reference in their entirety.

BACKGROUND OF THE INVENTION

1. Field of the Invention

The present invention relates to an enzyme, BgaC protein having beta-galactosidase (EC 3.2.1.23) activity derived from *Streptococcus pneumoniae*, and a method for using the same.

2. Description of the Related Art

Beta-galactosidase is a cleavage enzyme that belongs to family 35 of glycohydrolases, and that is found in plants and animals, as well as in a wide variety of microorganisms such as yeasts, fungi, bacteria, and archaea. Beta-galactosidase hydrolyzes lactose and its structurally related compounds, and additionally catalyzes transgalactosylation reactions of various beta-D-galactopyranosides including lactose. The hydrolase and transferase activities of beta-galactosidase have certain industrial applications (Nkayama and Amachi, 1999; Hung and Lee, 2002). Beta-galactosidase is widely used in the hydrolysis of lactose, which is present in milk products such as milk and whey, to glucose and galactose. The hydrolysis process is a fundamental method for reducing the lactose content employed in the food and dairy industries (Greenberg and Mahoney, Process Biochem. 16: 2-8, 1981; Gekas and Lopez-levia, 20: 2-12, 1985).

Meanwhile, many studies have been made on the relationship between the structure and function of a sugar chain in order to investigate its biological meaning and role, which has attracted a great deal of interest in the field. For these studies, there is a need for analysis of each sugar chain at the level of linkage specificity. In general, for the analysis of a component or sequence of a sugar chain, equipment such as HPLC and mass spectrometry has been widely used. However, a linkage-specific glycosidase is essentially needed for linkage-specifically analyzing the structure of a sugar chain. Therefore, there is a trial that employs a beta-galactosidase having linkage-specific glycosidase activity for analyzing the structure of a sugar chain.

Further, with respect to cancer treatment, there are a variety of treatment methods, such as chemotherapy administrating various anti-cancer agents, immunotherapy promoting antibody production against cancer cells, surgical therapy removing cancer cells, and radiation therapy killing cancer cells by irradiating radioactive rays. However, even though the primary cancer may be eradicated by such processes, some problems may still exist. That is, cancer may be a malignant tumor because of its metastatic ability, and in many cases, metastatic cancer is more likely to cause death. It cannot be said yet that a method for inhibiting the metastasis of cancer cells has been established, and a medicine having the effects of inhibiting the metastasis of cancer cells has not yet been commercially available. On the other hand, several steps are considered for the metastasis mechanism, and a casual relationship between the cancer metastasis and the sugar chain has been recently discussed in academic meetings. In the metastasis of cancer cells, cancer cells are first released from a cancer-developed site, and then move through the blood stream in a human body. E-selectin, which is one of the intercellular adhesive molecules, is expressed on the surface of an intravascular endothelial cell for several reasons. This E-selectin interacts with free cancer cells moving through the blood stream in the human body, and causes a rolling phenomenon, in which the free cancer cells roll on the surfaces of the intravascular endothelial cells and reduce their moving speed in the blood. Consequently, the free cancer cells adhere to the intravascular endothelial cells, and then pass through the intravascular endothelial cells. Thus, the cancer cells enter the vascular tissue, resulting in the formation of a new cancer cell nest.

In this series of steps, the adhesion between the E-selectin, which is one of the intercellular adhesive molecules expressed on the surface of the intravascular endothelial cell, and the sugar chains, which are present on the surfaces of cancer cells, plays a very important role in an initial stage of the adhesion between the cancer cells and the intravascular endothelial cells. As a sugar chain antigen on the surface of cancer cells, which interacts with the E-selectin, a sialic acid-containing complex sugar chain, called as Sialyl Lewis X (sLe$^x$) and Sialyl Lewis A (sLe$^a$), has been identified. That is, there is a report that the sugar chain acts as a ligand involved in the metastasis of cancer cells (Takada et al., Cancer Res. 53: 354-361, 1993). In the sugar chains, galactose-beta1,3-N-acetylglucosamine (Gal-β1,3-GlcNAc) is a core polysaccharide of sLe$^a$, and galactose-beta1,3-N-acetylglucosamine and galactose-beta1,3-N-acetylgalactosamine (Gal-β1,3-GalNAc) are major components of mucin-type and complex-type glycoproteins. Accordingly, a specific galactosidase capable of cleaving the terminal galactose at beta1,3 linkage is needed for inhibiting metastasis.

It has been known that BgaC protein has an activity of cleaving non-reducing terminal galactose linked by beta1,3 glycosidic linkage. However, BgaC proteins, which are galactosidases capable of cleaving the galactose linked by beta1,3-linkage, have not been well known, until now. Among the proteins, there is no enzyme that specifically recognizes a sugar followed by a galactose to cleave the galactose.

On the other hand, when an infectious microorganism invades a host cell, its glycosidase is involved in the cleavage of sugar chains exposed on the surface of the host cell. Therefore, the related genes are often found in pathogenic microorganisms. There is a report that a galactosidase having the activity of cleaving beta 1,4 linkage, which is designated as BgaA, was found in *Streptococcus pneumoniae* causing pneumonia. The *Streptococcus pneumoniae* BgaA is a putative 2,235-amino acid protein having a molecular weight of 247.3 kDa, which is present on the cell surface, and purified from culture medium (Zahner and Hakenberck, J. Bacteriol. 182: 5919-5921, 2000; Glasgow et al., J. Biol. Chem. 252: 8615-8623, 1977; Hughes and Jeanloz, Biochemistry, 10: 1535-1548, 1964).

The present inventors have analyzed the genomic information of *Streptococcus pneumoniae* that has already been disclosed (Hoskins et al., J. Bacteriol. 183: 5709-5712, 2001). As a result, it was found that another new putative nucleic acid molecule having galactosidase activity exists, thereby performing functional analysis of the nucleic acid molecule. Consequently, a novel cleavage enzyme, which has different sugar chain specificity from BgaA, was detected.

In particular, it was found that the novel enzyme selectively recognizes only the sugar chain having galactose-beta1,3-N-acetylglucosamine linkage, and hydrolyzes the galactose, which is useful for the functional analysis and modification of a sugar chain.

Further, it was observed that treatment of the enzyme inhibits the colony formation of cancer cells, which offers a possibility of using the enzyme as an anti-cancer agent, thereby completing the present invention.

SUMMARY OF THE INVENTION

It is an object of the present invention to provide a protein exhibiting beta1,3-galactosidase activity, which has an amino acid sequence represented by SEQ ID NO: 2 or an amino acid sequence having at least 90% homology therewith.

It is another object of the present invention to provide an isolated nucleic acid molecule encoding the protein.

It is still another object of the present invention to provide a recombinant vector containing the nucleic acid molecule.

It is still another object of the present invention to provide a transformant capable of expressing the beta1,3-galactosidase by introducing the recombinant vector.

It is still another object of the present invention to provide a method for selectively cleaving a non-reducing terminal galactose of galactose-beta1,3-N-acetylglucosamine using the beta1,3-galactosidase.

It is still another object of the present invention to provide a method for linkage-specifically analyzing the structure of a sugar chain by treating with an isolated beta-galactosidase of SEQ ID NO: 2, wherein the beta-galactosidase selectively hydrolyzes the galactose in the structure of galactose-β1,3-N-acetylglucosamine.

It is still another object of the present invention to provide a method for treating or diagnosing a disease, in which the sugar chain specifically occurred in the disease such as cancer is cleaved using the method for linkage-specifically cleaving the sugar chain.

It is still another object of the present invention to provide a method for inhibiting cancer cell growth using the protein.

BRIEF DESCRIPTION OF THE DRAWINGS

FIG. 3 is a drawing showing the result of measuring galactosidase enzyme activity of the BgaC protein, in which FIG. 3A is a graph showing enzyme activity and quantitative values, in the case of using ONPG (o-nitrophenyl-D-galactopyranoside) or PNPG (p-nitrophenyl-D-galactopyranoside) as a substrate for measuring BgaC enzyme activity;

FIG. 3B is a graph showing an optimal pH range for enzyme activity; and

FIG. 3C is a graph showing an optimal temperature range for enzyme activity.

DESCRIPTION OF THE PREFERRED EMBODIMENTS

The present invention relates to a novel beta-galactosidase derived from *Streptococcus pneumoniae* R6, and to a method for using the enzyme in modification and analysis of a sugar chain.

The present inventors used the genomic information of the *Streptococcus pneumoniae* R6 strain, which is a pathogenic microorganism, in order to find out a nucleic acid encoding a novel enzyme useful for sugar chain modification. In order to find out a nucleic acid that encodes an enzyme capable of modifying the sugar chain derived from a human, they screened *Streptococcus pneumoniae*, which is a pathogenic microorganism causing pneumonia, and could easily use the genome of R6 strain that has already been disclosed.

There is a report that *Streptococcus pneumoniae* R6 has a bgaA gene expressing a cell surface protein with beta1,4-galactosidase activity (Zahner and Hakenberck, J. Bacteriol. 182: 5919-5921, 2000). Another gene, bagC with putative beta-galactosidase activity has been known to exist by comparing the sequence homology. However, the specific activity and biochemical characteristics of the bgaC gene have not yet been reported.

Therefore, the present inventors amplified the gene designated as bgaC by polymerase chain reaction (PCR) using a chromosome of *Streptococcus pneumoniae* as a template, and cloned the gene, and isolated a nucleic acid molecule, so as to identify that the nucleic acid molecule has beta-galactosidase enzyme activity. The amino acid sequence of the identified nucleic acid was represented by SEQ ID NO: 2, and its DNA sequence was represented by SEQ ID NO: 1.

Accordingly, in one embodiment, the present invention relates to a nucleic acid molecule encoding the protein represented by SEQ ID NO: 2, or an nucleic acid molecule encoding a protein exhibiting beta-galactosidase enzyme activity with at least 90% homology therewith.

The term "homology", as used in relation to the beta-galactosidase gene derived from *Streptococcus pneumoniae* of the present invention, refers to sequence similarity with a DNA sequence of a wild type, and comprises a DNA sequence having preferably at least 90% homology with the DNA sequence encoding the beta-galactosidase of the present invention. The homology comparison was performed using comparison programs easily available. The commercially available computer programs can calculate the percentage of the homology (%) between two or more sequences, and homology (%) may be calculated over contiguous sequences.

Figure 1:
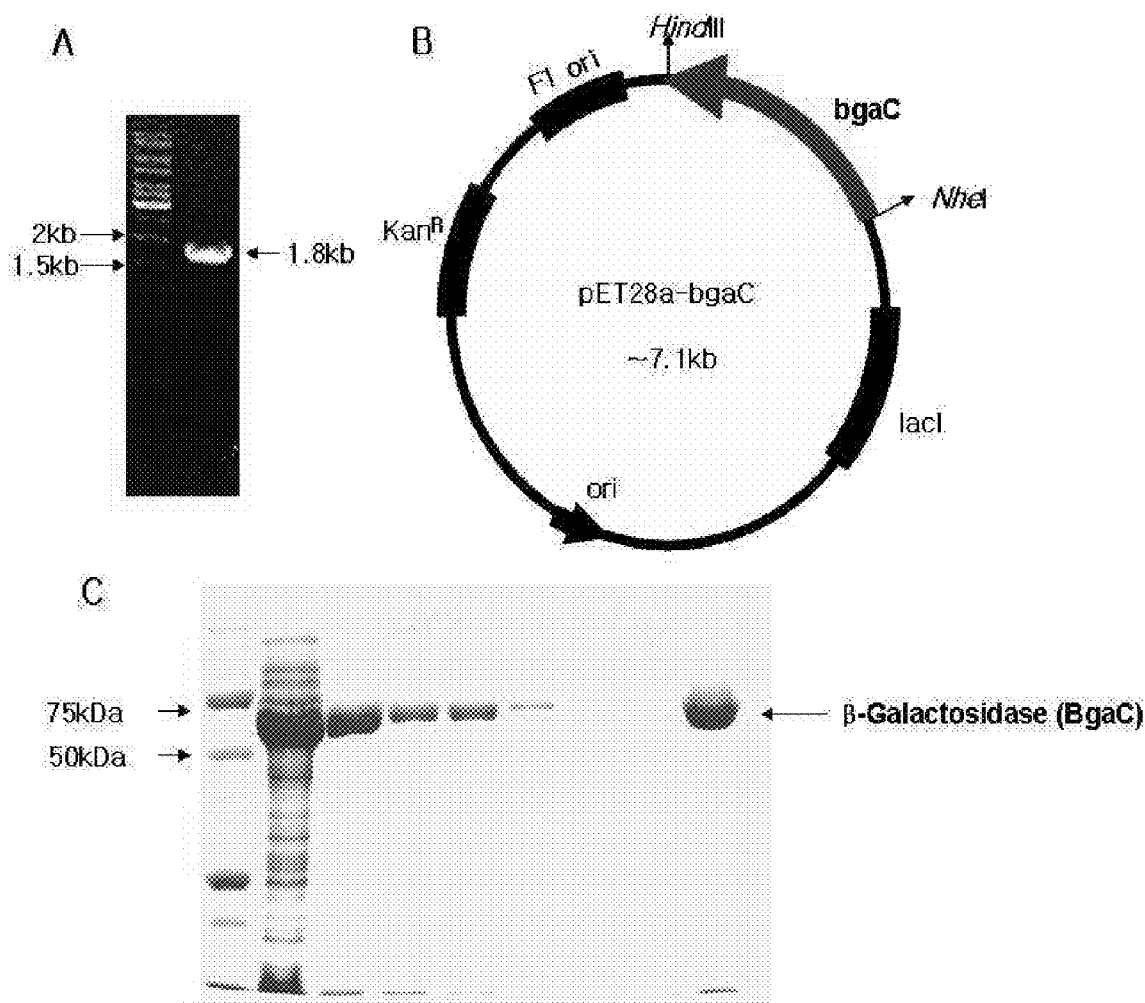
FIG. 1 is a drawing showing PCR amplification of a bgaC gene derived from *Streptococcus pneumoniae* (A), an expression vector cloning the same (B), and expression, isolation, and purification thereof (C).

In another embodiment, the present invention relates to an expression vector containing the nucleic acid molecule of the invention. The expression vector is preferably pET28a-bgaC cloned into the *E. coli* expression vector, pET28a (FIG. 1).

The term "vector" as used herein means any vehicle to allow DNA insertion into a host cell, and includes all of the typical vectors such as plasmid vector, cosmid vector, bacteriophage vector, and virus vector.

Further, the term "expression vector" as used herein means a vector expressing a target protein in a suitable host cell, and refers to a genetic construct including essential regulatory elements operably linked to express a gene insert.

In still another embodiment, the present invention relates to a host cell transformed with the expression vector. Transformation includes any method for introducing a nucleic acid molecule into an organism, a cell, a tissue, or an organ, and can be performed using the suitable standard technology selected according to the host cell, as disclosed in the art. Examples of the method include electroporation, protoplast fusion, calcium phosphate (CaPO$_4$) precipitation, calcium chloride (CaCl$_2$) precipitation, agitation with silicon carbide fiber, *agrobacterium*-mediated transformation, PEG, dextran sulfate, lipofectamine, or the like, but are not limited thereto.

The expression level and modification of the protein may vary depending on the host cell transformed, thus a very suitable host cell for the purpose can be selected and used. The host cell is preferably a prokaryotic cell, and preferred prokaryotic host cells include *Escherichia coli, Bacillus subtilis, Streptomyces, Pseudomonas, Proteus mirabilis*, and *Staphylococcus*, but are not limited thereto. Further, a lower eukaryotic cell such as a fungus (for example, *Aspergillus*) and a yeast (for example, *Pichia pastoris, Saccharomyces cerevisiae, Schizosaccharomyces, Neurospora crassa*) can be used.

In a preferred example of the invention, the cloned expression vector, pET28a-bgaC was transformed into *Escherichia coli* BL21 (DE3) strain (Novagen) (Deposit No.: KCTC 10956BP), and deposited at KCTC (Korean Collection for Type Cultures, Korea Institute of Bioscience and Biotechnology, 52, Ueun-dong, Yusung-gu, Daejeon-si, Korea) on Jun. 7, 2006.

The transformed host cell was cultured in a suitable medium to express a protein derived from *Streptococcus pneumoniae*, with beta-galactosidase activity, and the protein was isolated, purified to produce the protein exhibiting beta-galactosidase activity. The present inventors designated the protein, which is expressed from the bgaC gene derived from *Streptococcus pneumoniae* and has beta-galactosidase activity, as BgaC.

Accordingly, in still another embodiment, the present invention relates to the BgaC protein derived from *Streptococcus pneumoniae*, or the amino acid sequence represented by SEQ ID NO: 2, or the protein exhibiting beta-galactosidase enzyme activity with at least 90% homology therewith.

More particularly, the beta-galactosidase of the protein was derived from *Streptococcus pneumoniae*, and produced by recombinant DNA technology, in which the beta-galactosidase has a) maximum activity in the range of 20 to 40° C., b) maximum activity in the pH range of 5.0 to 8.0, c) a molecular weight of 50 to 100 kDa, d) more reactivity and higher substrate specificity to PNPG than to ONPG, and has a function of linkage-specifically cleaving the sugar chain.

Figure 3:
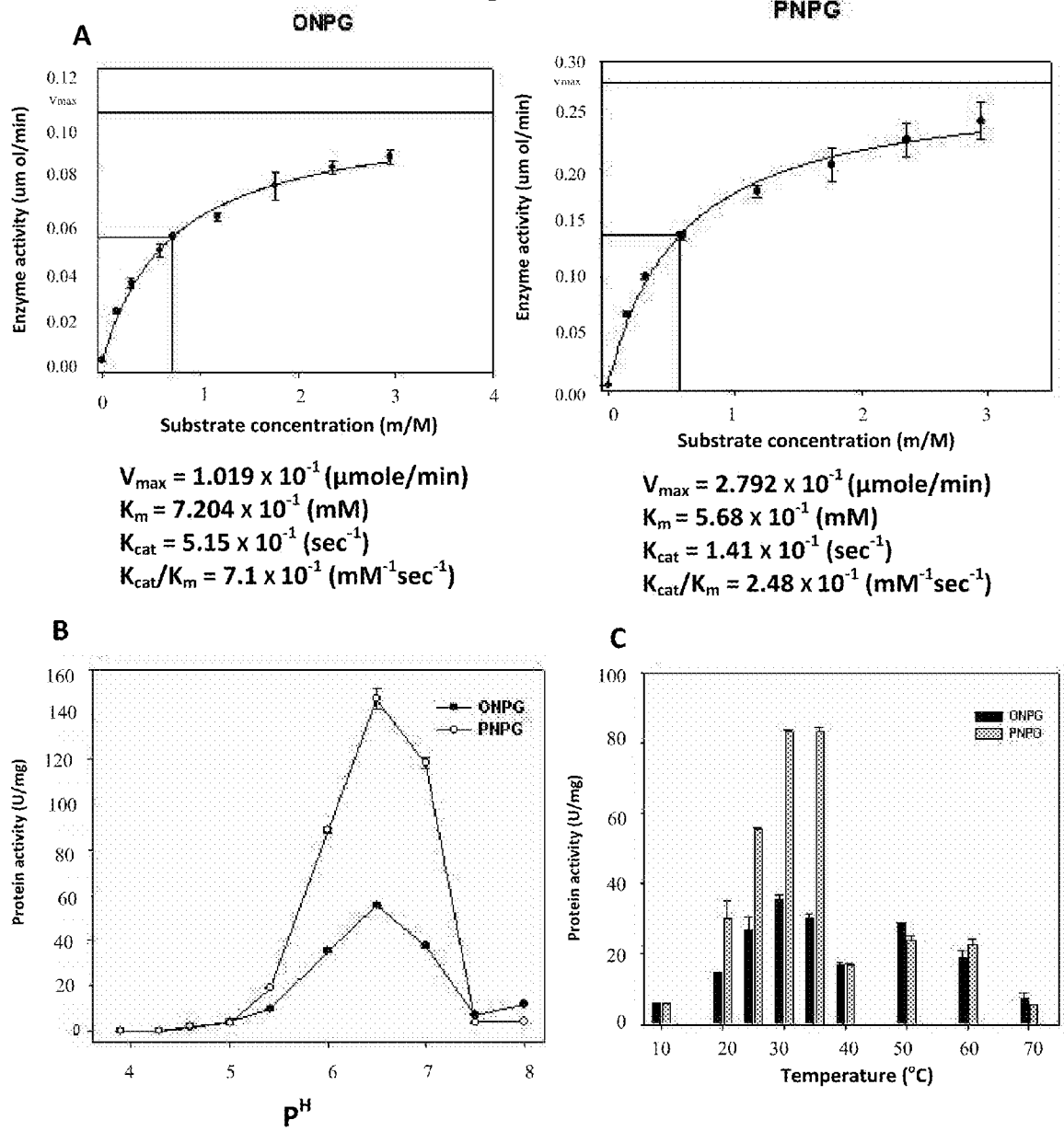

The beta-galactosidase enzyme activity of the protein was analyzed using ONPG (o-nitrophenyl-D-galactopyranoside) and PNPG (p-nitrophenyl-D-galactopyranoside) as a substrate. As a result, it was found that the BgaC protein derived from *Streptococcus pneumoniae* has higher activity on PNPG than ONPG (FIG. 3). Further, in order to determine the optimal pH for the BgaC protein, its enzyme activity was measured. Furthermore, in order to analyze the change in the enzyme activity depending on temperature, its enzyme activity was measured over wide ranges of temperatures. Consequently, it was found that the BgaC protein has maximum activity at pH 6.5, and in the temperature range of 30 to 35° C. (Example 4).

In still another embodiment, the present invention relates to the beta-galactosidase that selectively hydrolyzes galactose-beta1,3-N-acetylglucosamine, and the protein is preferably BgaC.

In order to analyze the characteristic of BgaC protein recognizing a sugar chain, a galactose cleavage test was performed using a variety of complex sugar chains as the substrate. As a result, it was found that the BgaC protein selectively cleaves only the non-reducing terminal galactose linked by beta1,3-glycosidic linkage. In particular, the protein was found to be specific to the sugar followed by the beta1,3-glycosidic linkage. More particularly, in the case where the sugar followed by the beta1,3-glycosidic linkage is N-acetylgalactosamine (GalNAc), the protein cannot cleave the terminal galactose. In the case where the sugar followed by the beta1,3-glycosidic linkage is N-acetylglucosamine (GlcNAc), the protein can cleave the terminal galactose. From the experimental results, it can be seen that the BgaC protein selectively cleaves the non-reducing terminal galactose in the structure of galactose-β1,3-N-acetylglucosamine.

In still another embodiment, the present invention relates to a method for linkage-specifically cleaving the galactose and modified sugar chain linked to galactose-beta 1,3-N-acetylglucosamine using the beta-galactosidase.

The method for linkage-specifically cleaving the galactose linked to galactose-beta 1,3-N-acetylglucosamine using the BgaC protein can be useful for the structural analysis of the sugar chain. For the analysis of the component or sequence of the sugar chain, a HPLC or mass spectrometry has been widely used. However, for the structural analysis of linkage specificity, a linkage-specific glycosidase is required. In particular, the glycosidase specific to the sugar followed by glycosidic linkage is more useful for the structural analysis. Until now, beta-galactosidases specific to galactose beta1,3 linkage has been known to exist. However, the BgaC protein of the present invention is the first beta1,3 galactosidase specific to the galactose followed by N-acetylglucosamine.

In still another embodiment, the present invention provides a method for linkage-specifically analyzing the structure of a sugar chain, wherein a galactose and modified sugar chain linked to galactose-β1,3-N-acetylglucosamine are treated with an isolated beta-galactosidase of SEQ ID NO: 2, and wherein the beta-galactosidase selectively hydrolyzes the galactose in the structure of galactose-β1,3-N-acetylglucosamine.

Preferably, the beta-galactosidase has the following characteristics of (a) to (d):

(a) maximum activity in the temperature range of 20 to 40 C.;

(b) maximum activity at a pH range of 5.0 to 8.0;

(c) a molecular weight of 50 to 100 kDa; and (d) more reactivity and higher substrate specificity to p-nitrophenyl-D-galactopyranoside (PNPG) than to o-nitrophenyl-D-galactopyranoside (ONPG).

Preferably, the beta-galactosidase the beta-galactosidase was isolated and purified from a medium, wherein a transformant transformed by an expression vector shown in FIG. 1B is cultured in the medium.

Preferably, wherein the beta-galactosidase was isolated and purified from a medium, wherein a transformant which has a deposit number of KCTC10956BP is cultured in the medium.

In still another embodiment, the present invention provides a method for treating or diagnosing a disease, in which the specific sugar chains present in cancer are cleaved using the BgaC protein having galactose cleavage activity specific to galactose-beta1,3-N-acetylglucosamine.

In still another embodiment, the present invention provides a possibility of using the BgaC protein as an anti-cancer agent or a tumor inhibitor, based on the ability of inhibiting the colony formation of cancer cells.

An sLe$^a$ sugar chain has been known to be excessively expressed on the surface of cancer cells. The sLe$^a$ sugar chain has a core structure of galactose-beta1,3-N-acetylglucosamine (Gal-β1,3-GlcNAc). Therefore, if the BgaC protein of the invention is used, the galactose of sLe$^a$ or Le$^a$ sugar chain can be selectively cleaved, so as to prevent cancer progression.

Hereinafter, the present invention will be described in more detail with reference to Examples. However, these Examples are for illustrative purposes only, and the invention is not intended to be limited by these Examples.

EXAMPLE 1

Amplification of bgaC Gene from *Streptococcus pneumoniae*

A *Streptococcus pneumoniae* chromosome was isolated from *Streptococcus pneumoniae* (ATCC BBA-255D) using a known phenol extraction (Ushiro et al., J Dent Res 70: 1422-1426, 1991). Polymerase chain reaction (PCR) was performed using the extracted chromosomal DNA as a template, and a pair of primers, bgaC-N(cgctagCATGACAC-GATTTGAGATACGAG; SEQ ID NO:3) and bgaC-C (ggaagcttTCATAAGTTTTCCCCCTTTATATG; SEQ ID NO:4), at which NheI and HindIII enzyme restriction sites were artificially inserted, so as to prepare a DNA fragment containing bgaC with a size of 1.8 kb (see FIG. 1A).

Figure 2:
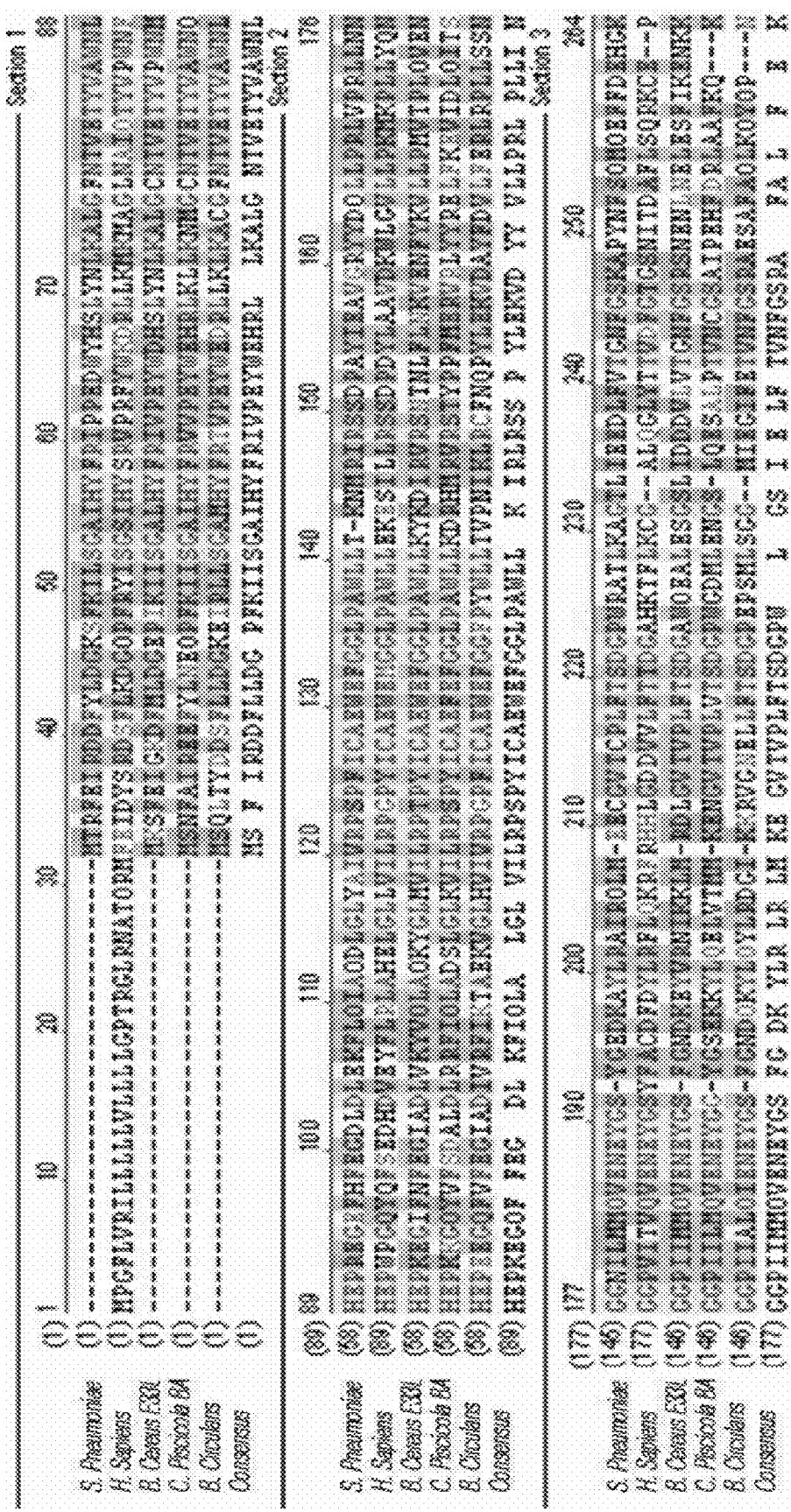
FIG. 2 is a drawing comparing homology and similarity among amino acid sequences of a BgaC protein derived from *Streptococcus pneumoniae*, a galactosidase from *Homo sapiens*, and BgaC proteins from *Bacillus cereus* E33L, *Carnobacterium piscicola* BA, and *Bacillus circulans*.
Figure 2:
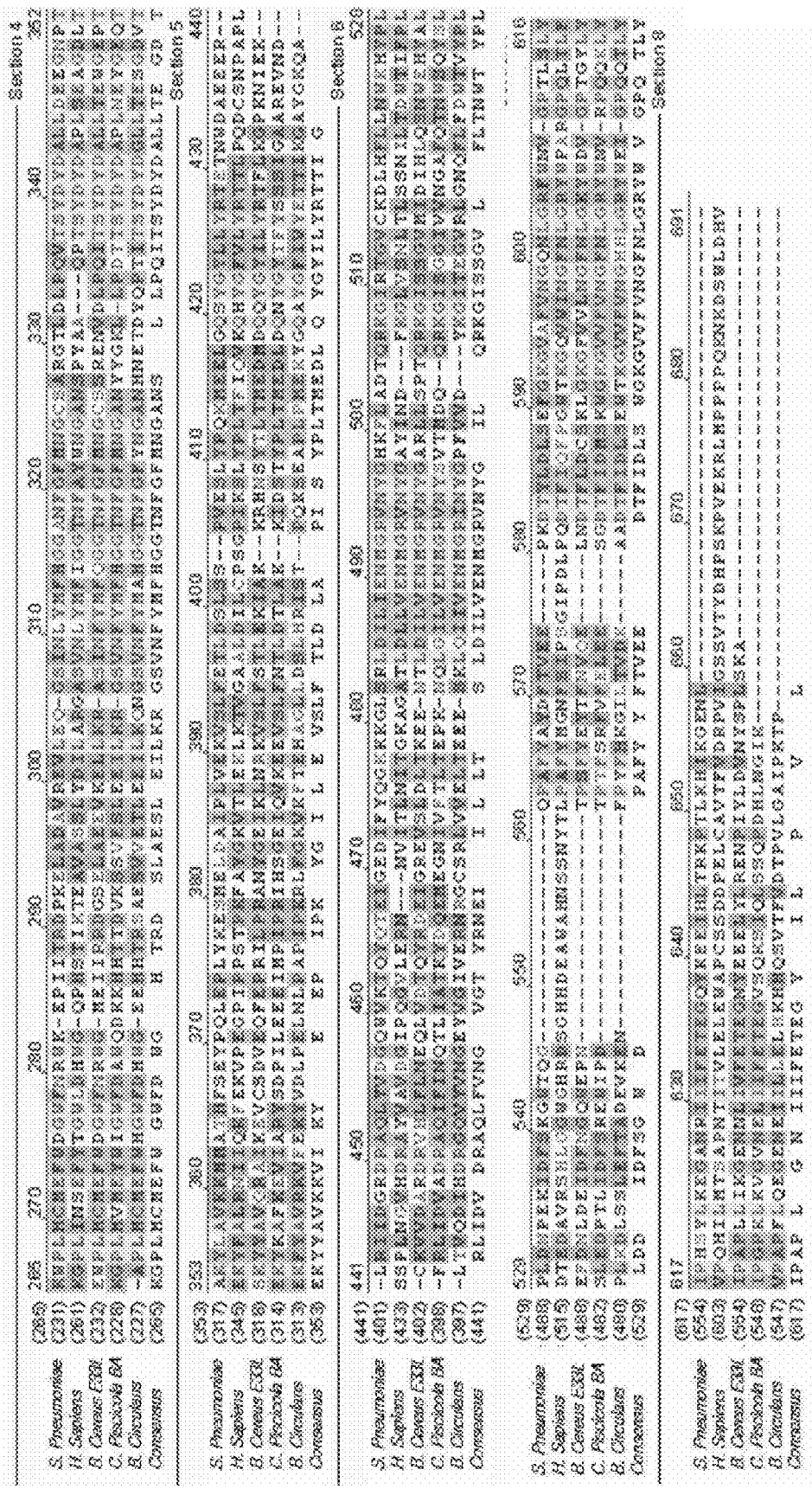

The base sequence of the prepared DNA fragment was translated. As a result, it was found that the *Streptococcus pneumoniae* bgaC gene encodes an intracellular protein consisting of 595 amino acids. From the result of translating into the amino acid sequence, it was found that the *Streptococcus pneumoniae* BgaC protein has 29.8%, 54.3%, 65.4%, and 46.7% homologies and 40.8%, 58.1%, 41.6%, and 54.2% similarities with *Homo sapiens* galactosidase, the BgaC proteins of *Bacillus cereus* E33L, *Carnobacterium piscicola* BA, and *Bacillus circulans*, respectively (see FIG. 2).

EXAMPLE 2

Large-Scale Expression, Isolation, and Purification of BgaC Protein

A recombinant vector pET28a (Novagen) was cleaved with NheI and HindIII restriction enzymes, and the PCR product, which was treated with the same enzymes and amplified as in Example 1, was introduced into the vector (FIG. 1B). The prepared recombinant vector was transformed into the *E. coli* BL21 (DE3) strain. The transformed *E. coli* was precultured in 5 ml of LB liquid medium (1% Bacto Tripton, 1% Sodium chloride, 0.5% Yeast extract) at 37° C. for 16 hours. The precultured medium was inoculated into fresh LB medium at a dilution of 1:100, and cultured at 37° C. When the absorbance of the medium was 0.4 to 0.6 at 600 nm, IPTG (isopropyl thiogalactoside) was added thereto to be a final concentration of 1 mM. Thus, BgaC protein expression was induced and the medium was cultured at 18° C. for 24 hours. The cultured *E. coli* cells were centrifuged, recovered, and then disrupted by sonication. The disrupted cells were centrifuged, and the supernatant was taken to be purified by affinity chromatography with nickel-nitrilotriacetic acid column, so as to obtain the 69 kDa BgaC protein (see FIG. 1C).

EXAMPLE 3

Galactosidase Activity Test for BgaC Protein

The basic activity of the BgaC protein was confirmed using ONPG (o-nitrophenyl-D-galactopyranoside) and PNPG (p-nitrophenyl-D-galactopyranoside) as a substrate. 2.2 mg of BgaC protein was mixed with a reaction mixture [90 mM sodium phosphate (NaPO$_4$) (pH 6.5), 10 mM magnesium chloride (MgCl$_2$), 45 mM beta-mercaptoethanol, 0.3 mM ONPG or PNPG] to be 300 μl, and reacted at 30° C. for 30 minutes. Then, its absorbance was measured at 420 nm to determine the amount of ONP (o-nitrophenol) or PNP (p-nitrophenol) produced. The activity of BgaC protein (Unit) was defined as ability to convert 1 nmole of ONPG or PNPG into ONP or PNP at 30° C. for 1 minute. The maximum reaction rate of the enzyme is 2.6 times higher in the case of using PNPG than in the case of using ONPG as the substrate. Further, the substrate affinity of the enzyme is 3.5 times stronger for PNPG than for ONPG (see FIG. 3A). In accordance with the Example, it was found that the BgaC protein has more reactivity and higher substrate specificity to PNPG than to ONPG.

EXAMPLE 4

Determination of Optimal pH and Temperature for BgaC Protein Activity

In order to determine an optimal range of hydrogen ion concentration (pH) for maximum enzyme activity, the enzyme activity of the BgaC protein was measured at various ranges of pH, that is, at the pH range of 3.89 to 8. A sodium acetate buffer was used to adjust pH 6 or less, and a sodium phosphate buffer was used to adjust pH 6 or more. Beta-galactosidase activity was measured using ONPG or PNPG as the substrate only with changing pH of the buffer solution (3.89, 4.28, 4.6, 5, 5.41, 6, 6.5, 7, 7.5, and 8) among reactants. The BgaC enzyme was found to have maximum activity at pH 6.5 (see FIG. 3B). In order to measure the change in enzyme activity of the BgaC protein according to temperature, the enzyme activity of the BgaC protein was measured in various ranges of temperature. As a result, the BgaC enzyme was found to have maximum activity in the temperature range of 30 to 35° C. (see FIG. 3C).

EXAMPLE 5

Analysis of Sugar Chain Specificity and Activity of BgaC Protein

Figure 4A:
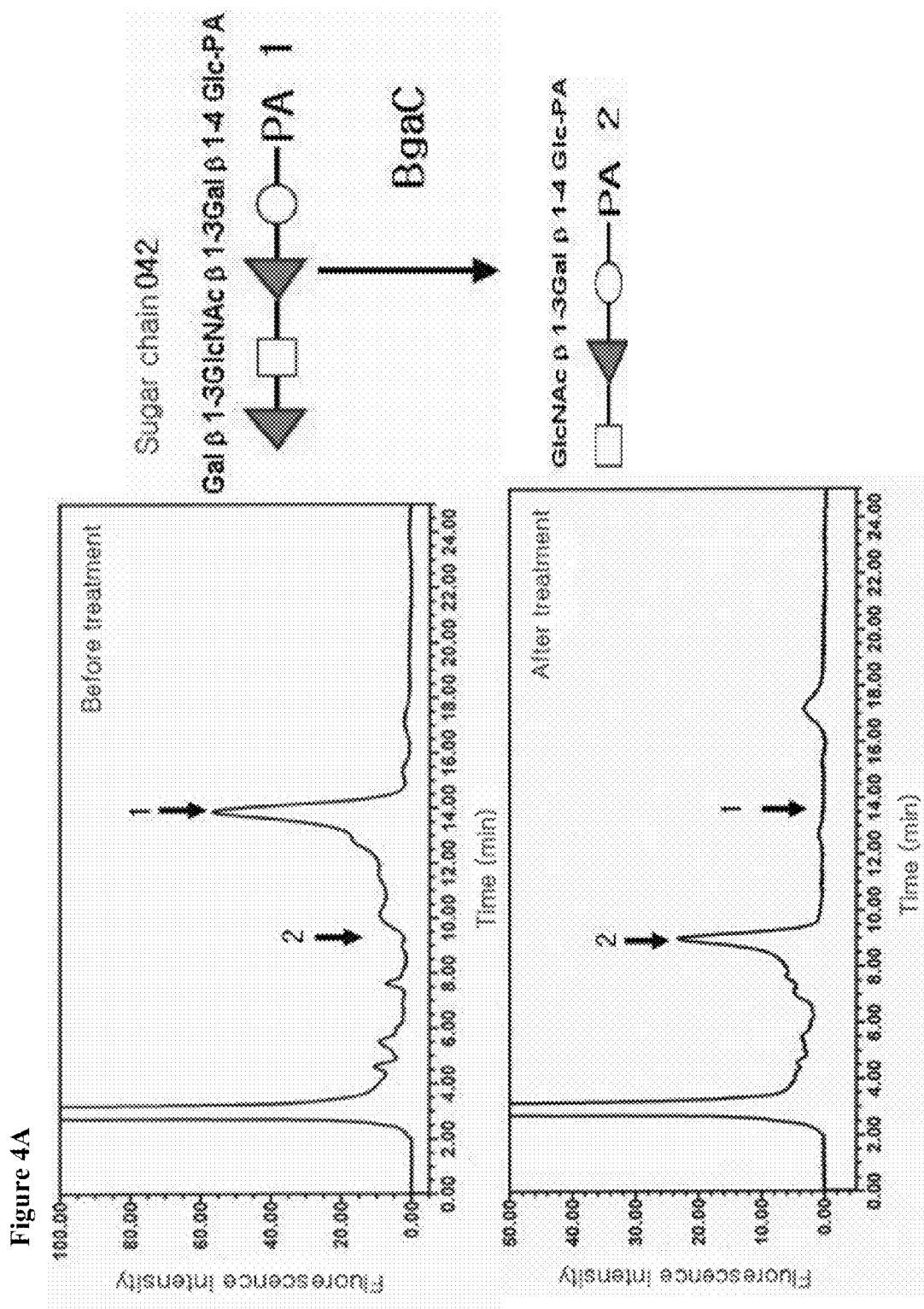
FIG. 4 is a drawing showing the result of measuring the specificity and cleavage activity of the BgaC protein derived from *Streptococcus pneumoniae* for the sugar chain, in which the protein specifically recognizes and cleaves the sugar chain of galactose-beta1,3-N-acetylglucosamine (Galactose-β1,3-GlcNAc) (A), whereas the protein does not cleave the galactose linked to N-acetylgalactosamine (GalNAc) (B), and the non-reducing terminal galactose linked by beta1,4 glycosidic linkage, instead of beta1,3 glycosidic linkage (C).
Figure 4B:
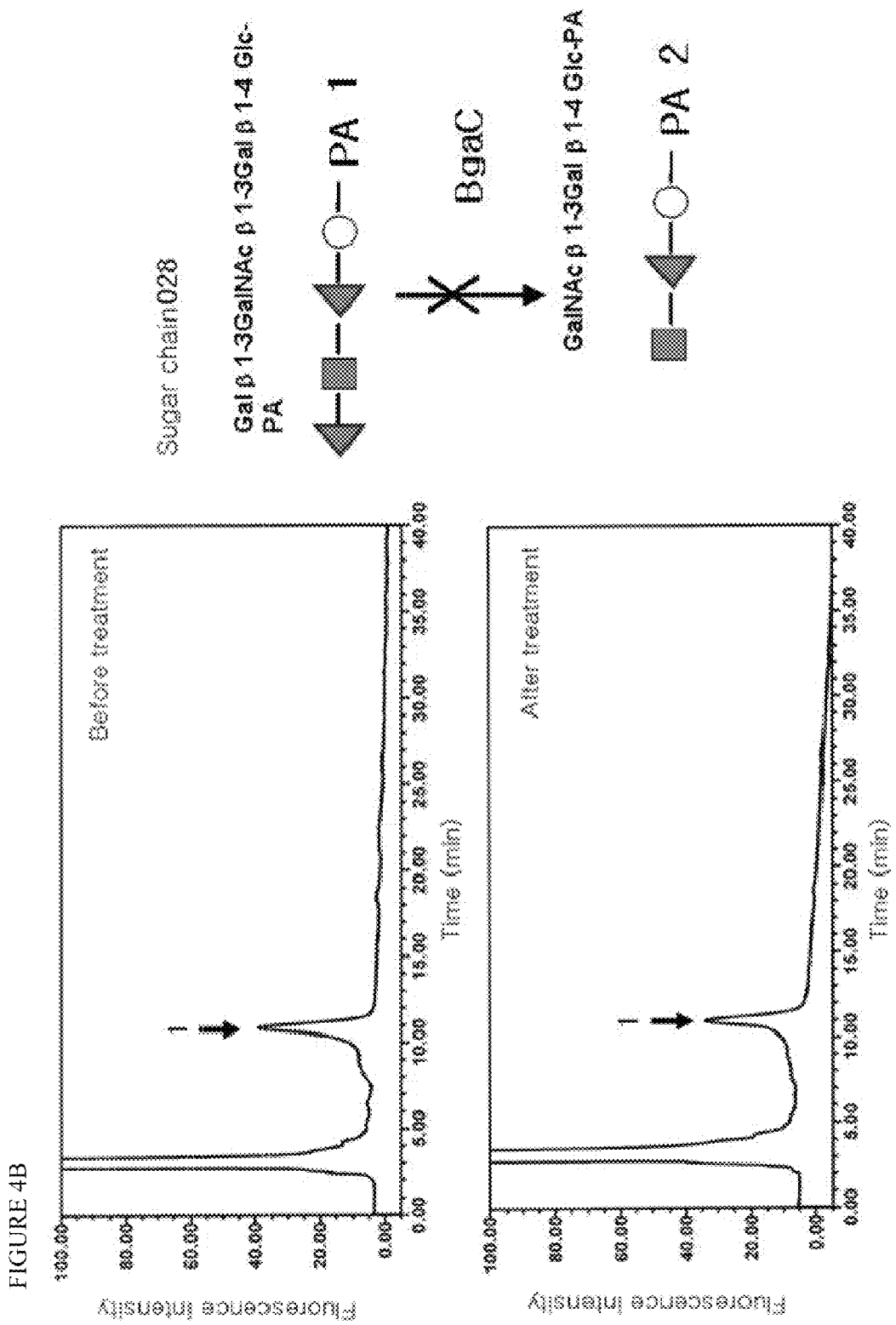
Figure 4C:
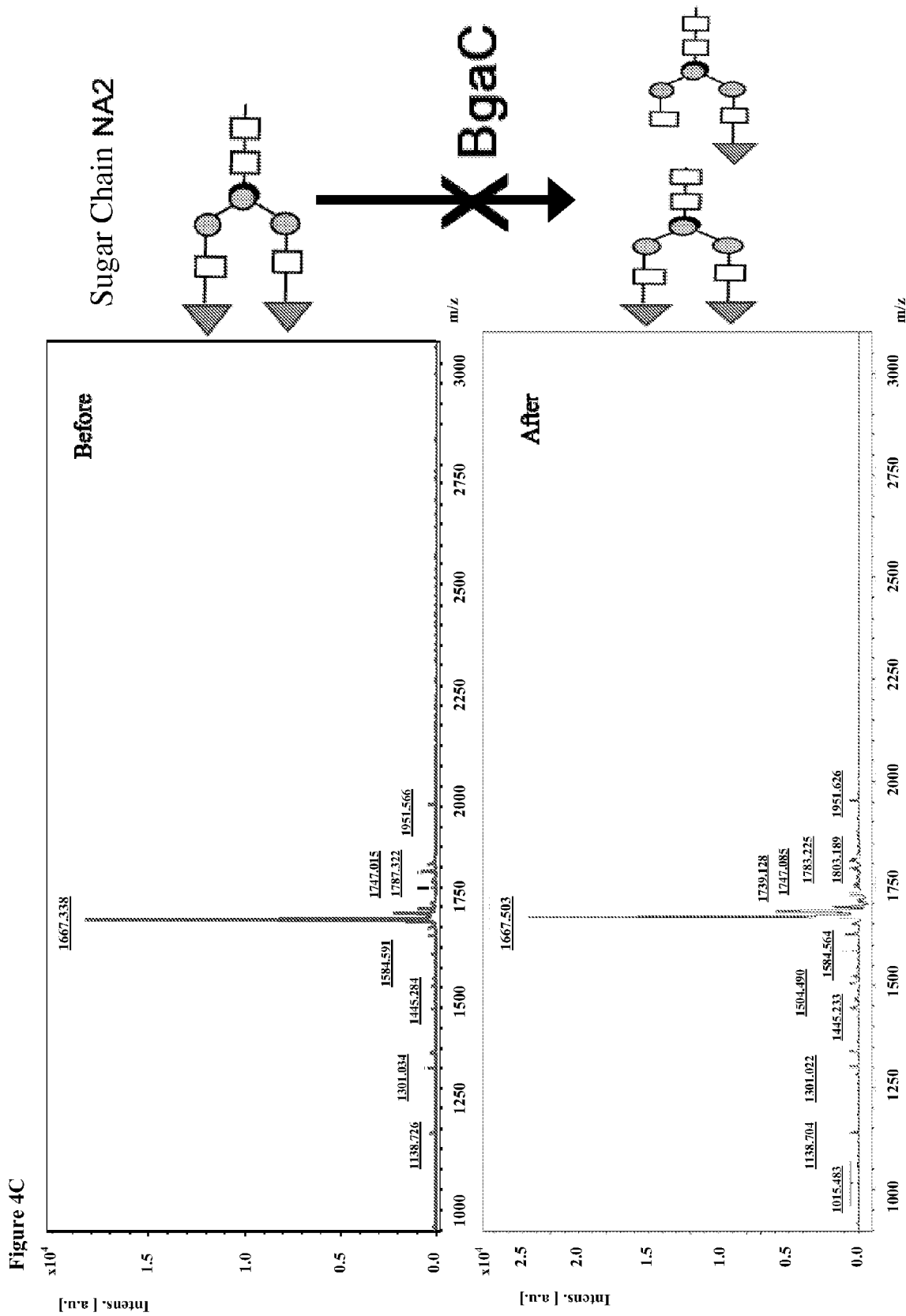

Substrate specificity of the BgaC protein was analyzed using sugar chains 042, 028 purchased from Takara Co. (Japan) and NA2 sugar chain [Mannotriose-di-(N-acetyl-D-glucosamine)] purchased from Sigma. The sugar chains from Takara Co. are sugar chains labeled with fluorescence, and thus a HPLC from Waters Co. (USA), which is equipped with fluorescence detector, was used. The sugar chain from Sigma is a sugar chain not labeled with fluorescence, and thus a microflex from Bruker Co. (Germany), which is a MALDI-TOF mass spectrometry, was used to analyze a mass change. FIG. 4A is the result of HPLC analysis by treating the sugar chain 042 (Gal-β1,3-GlcNAc-β1,3-Gal-β1,4-Glc-PA) from Takara with the BgaC protein. The BgaC protein hydrolyzed the non-reducing terminal galactose of the sugar, so as to give a peak of GlcNAc-β1,3-Gal-β1,4-Glc-PA as a product, in which the galactose was removed. FIG. 4B is the result of treating the sugar chain 028 (Gal-β1,3-GalNAc-β1,3-Gal-β1, 4-Glc-PA) from Takara with the BgaC protein, in which the terminal galactose of the sugar was found not to be removed. FIG. 4C is the result of MALDI-TOF analysis by treating the sugar chain NA2 from sigma with the BgaC protein. The sugar chain NA2 has a bi-antennary structure with two branches, in which the non-reducing terminal portion is Gal-β1,4-GlcNAc-β1,3-Man. It was found that the BgaC protein cannot cleave the terminal galactose linked by beta1,4 glycosidic linkage.

EXAMPLE 6

Ability of BgaC Protein to Inhibit Colony Formation of Cancer Cells

Figure 5:
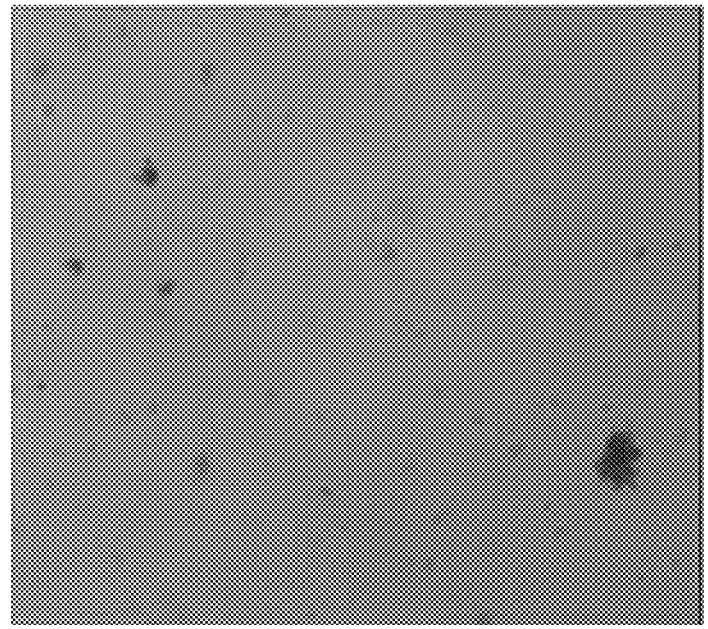
FIG. 5 is a drawing showing the effect of the BgaC protein on the colony formation of cancer cells, in which the colony formation is inhibited when the cancer cells are treated with the BgaC protein, as compared with the cancer cells not treated with the BgaC protein, thereby offering the possibility of using the BgaC protein for cancer cell growth inhibition.
Figure 5:
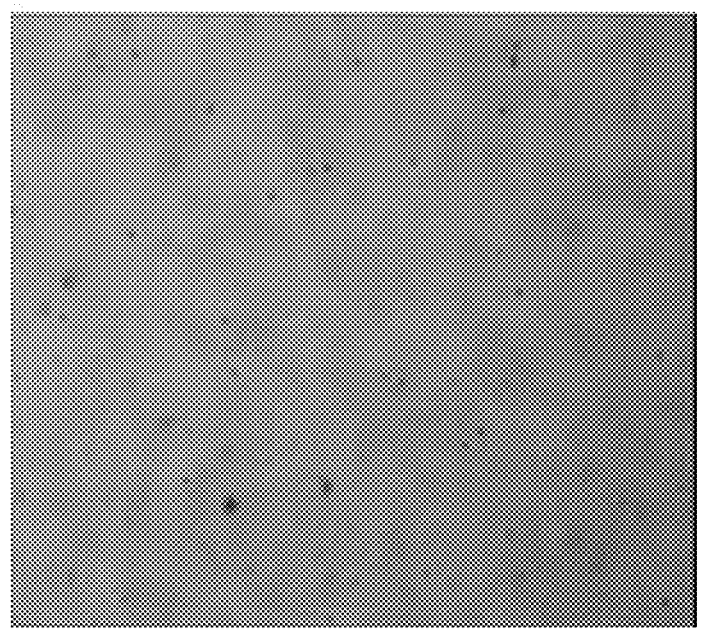

In order to induce the overexpression of RAS protein, which is involved in tumor development, a fibroma cell line, NIH3T3 transfected with ras gene was inoculated into a 10 mm culture plate, in which Dulbecco's modified eagle's medium (DMEM) containing 20% fetal bovine serum and 300 unit of the BgaC protein was placed, and cultured at 37° C. with 5% $CO_2$. The overexpression of ras gene promotes the colony formation of NIH3T3 cells. The colony formation of NIH3T3 cells, which had been treated with the BgaC protein, was inhibited, as compared with that of NIH3T3 cells that had not been treated with the BgaC protein (see FIG. 5). The colony formation is a general characteristic of cancer cells. Sialyl Lewis A (sLe$^a$), which is a Lewis antigen acting as a ligand involved in the metastasis of cancer cells, is a sugar chain formed by galactose-beta1,3-N-acetylglucosamine (Gal-β1,3-GlcNAc) linkage (Takada et al., Cancer Res. 53: 354-361, 1993). Accordingly, the experimental result indicates that the BgaC protein blocked the formation of Lewis A antigen, so as to reduce the metastasis of cancer cells, and thus the colony formation was inhibited. The colony formation of cancer cells was inhibited by the BgaC activity, which offers a possibility of using the BgaC protein as an anti-cancer agent or a tumor inhibitor.

EFFECTS OF THE INVENTION

As described above, the beta-galactosidase, BgaC protein can linkage-specifically cleave a sugar chain, complex sugar, and oligosaccharide containing galactose-beta1,3-N-acetylglucosamine, thereby being useful for linkage-specific analysis of the sugar chains. Further, the specific sugar chains are selectively cleaved using the BgaC protein having the galactose cleavage activity specific to the sugar chains, which offers a possibility of using the protein medically or diagnostically such as an anti-cancer agent or a tumor inhibitor. Thus, the present invention is very useful for the pharmaceutical industry.

What is claimed is:

1. A method for analyzing the structure of a sugar chain, comprising:
   a) treating the sugar chain with a beta-galactosidase of SEQ ID NO:2;
   b) detecting whether the beta-galactosidase cleaves a galactose from the sugar chain; and
   c) determining that the sugar chain has a non-reducing terminal galactose linked to N-acetylglucosamine (GlcNAc) by beta 1,3-glycosidic linkage when the beta-galactosidase cleaves the galactose from the sugar chain.

2. The method according to claim 1, wherein the beta-galactosidase has the following characteristics (a) to (d):
   (a) maximum activity in the temperature range of 20 to 40° C.;
   (b) maximum activity at a pH range of 5.0 to 8.0;
   (c) a molecular weight of 50 to 100 kDa; and
   (d) more reactivity and higher substrate specificity to p-nitrophenyl-D-galactopyranoside (PNPG) than to o-nitrophenyl-D-galactopyranoside (ONPG).

3. The method according to claim 1, wherein the beta-galactosidase was isolated and purified from a medium, wherein a transformant transformed by an expression vector shown in FIG. 1B is cultured in the medium.

4. The method according to claim 1, wherein the beta-galactosidase was isolated and purified from a medium, wherein a transformant which has a deposit number of KCTC10956BP is cultured in the medium.

* * * * *